US007335647B2

(12) United States Patent
Egashira et al.

(10) Patent No.: US 7,335,647 B2
(45) Date of Patent: Feb. 26, 2008

(54) DRUGS FOR LIVER DISEASES

(75) Inventors: Kensuke Egashira, 101, 3-5-2, Momochihama, Sawara-ku, Fukuoka-shi (JP) 814-0001; Akira Takeshita, Onojo-shi (JP); Masamichi Koyanagi, Beppu-shi (JP); Makoto Nakamuta, Fukuoka-shi (JP); Ken-ichi Nishida, Tokyo (JP)

(73) Assignees: Kensuke Egashira, Fukuoka-shi (JP); Daiichi Sankyo Company, Limited, Tokyo (JP)

( * ) Notice: Subject to any disclaimer, the term of this patent is extended or adjusted under 35 U.S.C. 154(b) by 492 days.

(21) Appl. No.: 10/398,285

(22) PCT Filed: Sep. 28, 2001

(86) PCT No.: PCT/JP01/08552

§ 371 (c)(1),
(2), (4) Date: Apr. 10, 2003

(87) PCT Pub. No.: WO02/30464

PCT Pub. Date: Apr. 18, 2002

(65) Prior Publication Data

US 2005/0053603 A1    Mar. 10, 2005

(30) Foreign Application Priority Data

Oct. 11, 2000   (JP) .............................. 2000-310604

(51) Int. Cl.
A61K 31/70   (2006.01)
A01N 43/04   (2006.01)
C12P 19/34   (2006.01)
C07H 21/02   (2006.01)
C07H 21/04   (2006.01)

(52) U.S. Cl. .................... 514/44; 435/91.1; 536/23.1
(58) Field of Classification Search ................ 514/44; 435/91.1; 536/23.1
See application file for complete search history.

(56) References Cited

U.S. PATENT DOCUMENTS 5,399,346 A * 3/1995 Anderson et al. ......... 424/93.21
5,705,360 A * 1/1998 Rollins et al. ............ 435/69.1

FOREIGN PATENT DOCUMENTS

| JP | 8-119934 | 5/1996 |
| JP | 9-67399 | 3/1997 |
| JP | 11-60502 | 3/1999 |
| JP | 11-506005 | 6/1999 |
| JP | 2000-239182 | 9/2000 |
| WO | 95/13295 | 5/1995 |
| WO | 96/23068 | 8/1996 |
| WO | 96/38559 | 12/1996 |
| WO | 98/06703 | 2/1998 |
| WO | 99/07678 | 2/1999 |

OTHER PUBLICATIONS

Grove et al, Advanced Drug Delivery Reviews, 30:199-204, 1998.*
Prieto et al, Expert Opinion in Biological Therapeutics, 4:1073-1091, 2004.*
Prosser et al, World Journal of Gastroenterology, 12:509-515, 2006.*
Egashira et al, FASEB Journal, 14:1974-1978, 2000.*
Fujimoto, Journal of Gastroenterology and Hepatology, 15:D33-D36, 2000.*
Teizo Yoshimura et al.; "Purification and amino acid analysis of two human glioma-derived monocyte chemoattractants" The Journal of Experimental Medicine, vol. 169, pp. 1449-1459 Apr. 1989.
Kouji Matsushima et al.; "Purification and characterization of a novel monocyte chemotactic and activating factor produced by a human myelomonocytic cell line" The Journal of Experimental Medicine, vol. 169, pp. 1485-1490, Apr. 1989.
Teizo Yoshimura et al.: "Human monocyte chemoattractant protein-1 (MCP-1) full length cDNA cloning, expression in mitogen-stimulated blood mononuclear leukocytes, and sequence similarity to mouse competence gene JE" FEBS Lett., vol. 244, No. 2, pp. 487-493, Feb. 1989.
Israel F. Charo et al.: "Molecular cloning and functional expression of two monocyte chemoattractant of protein-1 receptors reveals alternative splicing of the carboxyl-terminal tails" Proc. Natl. Acad. Sci. USA, vol. 91, pp. 2752-2756, Mar. 1994.
Shinsuke Yamagami et al.: "cDNA cloning and functional expression of a human monocyte chemoattractant protein 1 receptor" Biochemical and Biophysical Research Communications, vol. 202, No. 2, pp. 1156-1162, Jul. 29, 2004.
Yu Jun Zhang et al.: "Structure/activity analysis of human monocyte chemoattractant protein-1 (MCP-1) by mutagenesis" The Journal of Biological Chemistry, vol. 269, No. 22, pp. 15918-15924, Jun. 3, 1994.
Teizo Yoshimura et al.: "Production and characterization of mouse monoclonal antibodies against human monocyte chemoattractant protein-1" The Journal of Immunology, vol. 147, No. 7, pp. 2229-2233 Oct. 1, 1991.
M.J. Czaja et al.: "Monocyte chemoattractant protein 1 (MCP-1) expression occurs in toxic rat liver injury and human liver disease" Journal of Leukocyte Biology, vol. 55, No. 1, pp. 120-126 1994
F. Marra et al.: "Monocyte chemotactic protein-1 as a chemoattractant for human hepatic stellate cells" HEPATOLOGY, vol. 29, No. 1, pp. 140-148, Jan. 1999.
F. Marra et al.: "Increased expression of monocyte chemotactic protein-1 during active hepatic fibrogenesis: correlation with monocyte Infiltration" American Journal of Pathology, vol. 152, No. 2, pp. 423-430 Dec. 5, 1996.

* cited by examiner

*Primary Examiner*—Valarie Bertoglio
*Assistant Examiner*—Wu-Cheng Winston Shen
(74) *Attorney, Agent, or Firm*—Oblon, Spivak, McClelland, Maier & Neustadt, P.C.

(57) ABSTRACT

Preventives and/or remedies for liver diseases, which comprise monocyte chemoattractant protein-I (MCP-I) function inhibitors as active ingredients, respectively. Administration of the MCP-I function inhibitors brings about effects in preventing and/or remedying liver diseases.

12 Claims, No Drawings

DRUGS FOR LIVER DISEASES

TECHNICAL FIELD

This invention relates to novel drugs for liver diseases, and also to a novel preventive and/or remedial method for liver diseases.

BACKGROUND ART

Chemokines are a group of proteins having migration activity for leukocytes and lymphocytes. From their structures, these chemokines can be divided roughly into four types. Those with the first and second cysteines arranged continuously are called "CC chemokines".

Monocyte chemoattractant protein-1 (MCP-1), one of the CC chemokines, was reported as a protein by itself, and at substantially the same time, its cDNA sequence was ascertained (J. Exp. Med., 169, 1449-1459, 1989; J. Exp. Med., 169, 1485-1490, 1989; FEBS lett., 244, 487-493, 1989).

Receptors which recognize MCP-1 have already been identified, and their cDNAs have also been cloned (Proc. Natl. Acad. Sci. USA, 91, 2752-2756, 1994; Biochem. Biophys. Res. Commun., 202, 1156-1162, 1994). Nine types of receptors are now known as CC chemokine receptors, and the MCP-1 receptor is called "CCR2".

Rollins et al. reported that they prepared a variety of amino acid mutants of MCP-1 protein and some of the amino acid mutants were found to have lost cell migration activity (J. Biol. Chem., 269, 15918-15924, 1994). Among these mutants, the mutant obtained by deleting the second to eighth amino acids as counted from the N terminal, that is, 7ND-MCP-1 has binding ability to CCR2, but does not provoke cell migration. As a dominant negative, on the other hand, 7ND-MCP-1 forms a dimer with wild-type MCP-1 and inhibits the function of MCP-1. Further, it is known that N-terminal deletions of chemokines are potent dominant negative inhibitors of chemokine-receptor interaction by forming heterodimers with the corresponding endogenous monomer of the chemokine and that these inhibitors are effective for the remedy of inflammations such as post-angioplasty restenosis, rheumatoid arthritis, inflammatory bowel disease, multiple sclerosis, and chronic pulmonary inflammation, e.g., pulmonary fibrosis; autoimmune disease; and the like (JP-A-11506005).

Fibrosis of the liver is a morbidity in which destruction of the normal tissue structure, proliferation of fibroblasts and accumulation of extracellular matrices advance, and cirrhosis is a post-fibrosis disease. At present, no effective and safe remedial method has been established yet for these diseases. For example, various symptomatic treatments have been applied to cirrhosis, but cirrhosis advances to uncompensated cirrhosis, resulting in poor prognostic improvements.

An object of the present invention is to provide a novel preventive and/or remedy for a liver disease such as hepatic fibrosis or cirrhosis and further, a novel preventive and/or remedial method for such a liver disease.

DISCLOSURE OF THE INVENTION

The present inventors have ascertained that 7ND-MCP-1 produced in myocytes by intramuscular injection of an expression vector containing 7ND-MCP-1 gene, into the femoral region of a model animal (rat) suppresses hepatic fibrosis and have found that MCP-1 function inhibitors are useful as preventives and/or remedies for liver diseases, leading to the completion of the present invention.

Described specifically, the present invention provides a preventive and/or remedy for a liver disease, comprising an MCP-1 function inhibitor as an active ingredient.

The present invention also provides a preventive and/or remedial method for a liver disease, which comprises administering a gene, which encodes an MCP-1 antagonist or an MCP-1 dominant negative, to an organism.

The present invention further provides a preventive and/or remedy composition for a liver disease, comprising an MCP-1 function inhibitor and a pharmaceutically acceptable carrier.

The present invention still further provides use of an MCP-1 function inhibitor for the manufacture of a preventive and/or remedy for a liver disease.

BEST MODE FOR CARRYING OUT THE INVENTION

No particular limitation is imposed on the MCP-1 function inhibitor for use in the present invention insofar as it can inhibit the function of MCP-1 in the organism. Specific examples can include anti-MCP-1-antibodies (including polyclonals and monoclonals), MCP-1 antagonists (including proteins and non-protein, low molecular compounds), MCP-1 dominant negatives (including proteins and non-protein, low molecular compounds), and, when those capable of inhibiting the function of MCP-1 are proteins, also genes encoding such proteins. As these antibodies, antagonists, dominant negatives, and encoding genes, a variety of antibodies, antagonists, dominant negatives and encoding genes are already known. Further, those available by methods known per se in the art are all usable in the present invention.

For example, anti-MCP-1 antibodies can be obtained by the procedure disclosed in J. Immunology, 147, 2229-2233, 1991, while MCP-1 antagonists and MCP-1 dominant negatives are known from JP-A-11506005 and the like.

In the present invention, introduction of a gene encoding an MCP-1 function inhibitor is more preferred than administration of the MCP-1 function inhibitor as a protein to an organism, because the former allows the gene to remain longer in the organism (blood).

In the present invention, MCP-1 antagonists or MCP-1 dominant negatives are preferred, with 7ND-MCP-1 being particularly preferred. Further, genes encoding MCP-1 antagonists or MCP-1 dominant negatives are preferred, with a gene encoding 7ND-MCP-1 being particularly preferred. As the gene encoding 7ND-MCP-1, DNA having the base sequence indicated by SEQ ID NO: 1 of the Sequence Listing can be used. This DNA can be prepared by a genetic engineering procedure known per se in the art. Described specifically, from the base sequence of a DNA encoding the wild-type MCP-1 and indicated by SEQ. ID. NO: 2 of the Sequence Listing, the DNA can be prepared using PCR which employs a synthesis primer.

No particular limitation is imposed on an expression vector to be used for the expression of the gene in an organism insofar as it can exhibit its function. Illustrative are plasmid vectors such as pcDNA3, pEF-BOS and pXT1; and retrovirus vectors such as adenovirus vectors and Sendaivirus vectors. Upon constructing an expression vector, it is also possible to use a promoter or an enhancer. No particular limitation is imposed on the promoter or an enhance insofar as it functions in a host (organism). Examples of the promoter can include SV40 promoter, CMV promoter, HSV-TK, SRα, and RSV.

To have the gene expressed in the host (organism), liposomes are also usable. In this case, the gene may exist inside the liposomes, or inside or outside the lipid bilayer membranes which constitute the liposomes. A variety of liposome compositions are known to permit the expression of the gene in the host (organism).

To confirm production of 7ND-MCP-1 protein from the 7ND-MCP-1 gene introduced, it is only necessary to determine by ELISA whether or not the protein exists in serum.

Administration of the MCP-1 function inhibitor, which is an active ingredient of the preventive and/or remedy according to the present invention for a liver disease, to organisms of animals including human being can be conducted orally or parenterally. When the function inhibitor is a protein, parenteral administration is desired. As a parenteral administration method, injection can be mentioned. Injection can be performed directly to a diseased part (the liver) or to a part other than the liver, such as an artery, vein, muscle, skin or subcutaneous tissue. As a pharmaceutical preparation (preparation forms) for injecting the MCP-1 function inhibitor, an injection can be mentioned. This injection can be obtained by known pharmaceutical preparation manufacturing technology. Upon manufacturing the injection, one or more of known additives to pharmaceutical preparations can be added. Illustrative are isotonicities, buffers, preservatives, excipients, and soothing agents.

The dosage to each patient can be adequately determined depending on his or her condition, age, sex, weight and the like. For example, 0.1 to 1,000 mg (in the case of a protein) or 0.01 to 100 mg (in the case of a gene) may be administered once in 2 to 4 weeks.

EXAMPLE

The present invention will next be described in further detail based on an example, although the present invention shall by no means be limited to the example.

(1) Construction and Expression of 7ND-MCP-1

A plasmid vector encoding 7ND-MCP-1 was prepared by PCR using the pCDNA3 vector plasmid which encodes MCP-1 as a template. Each mutation was confirmed by a DNA sequence analysis from both directions. The resultant PCR product encoding 7ND-MCP-1 was inserted into the multicloning site of the pcDNA3 vector plasmid, the vector plasmid was transformed in *Escherichia coli*, and then, the plasmid DNA was purified using "Plasmid Giga Kit" (QIAGEN GmbH).

(2) Effect of 7ND-MCP-1 on Dimethylnitrosamine-Induced Hepatic Fibrosis in Rats

Hepatic fibrotic model rats were prepared by intraperitoneally administering 1% dimethylnitrosamine (100 µL/100 g-rat weight) to male Wistar rats daily on three straight days a week for 4 weeks in total. Three days before administration of the mutated MCP-1 gene (7ND-MCP-1 gene), 0.25% bupivacaine hydrochloride (100 µL/100 g-rat weight) was intramuscularly injected to the right femoral muscles of the rats to conduct pretreatment for increased efficiency of gene introduction.

The mutated MCP-1 gene (7ND-MCP-1 gene) was intramuscularly injected (100 µg DNA [1 µg/1 µL]/100 g-rat weight) into the pretreated parts on the day of start of the dimethylnitrosamine administration. To a control group, the vector DNA was administered in the same amount. The mutated MCP-1 gene (7ND-MCP-1 gene) was readministered in the same amount as mentioned above to the left femoral muscles of the rats on the $12^{th}$ day of the dimethylnitrosamine administration. Further, three days before the readministration (on the $12^{th}$ day of the dimethylnitrosamine administration), the above-mentioned pretreatment with bupivacaine hydrochloride was applied likewise. To the control group, the vector DNA was also administered similarly.

Twenty-eight (28) days later, the liver was enucleated, and its weight, and levels of tissue fibrosis and tissue hydroxyproline were measured. The fibrosis level was determined by staining a fibrosed part in accordance with the Masson's trichrome staining. The level of tissue hydroxyproline was measured by HPLC.

As a result, the liver weight was 10.42±4.01 g ($p<0.05$ according to the Mann-Whitney significant test) and ± in the group administered with the mutated MCP-1 gene (7ND-MCP-1 gene) as opposed to 4.95±2.00 g in the control group, and the fibrosis level was ±, as opposed to +++ in the control group. A pronounced hepatic fibrosis inhibiting effect was observed.

The tissue hydroxyproline level was 28.2±9.12 µmol/g-rat liver weight ($p<0.05$ according to the Mann-Whitney significant test) in the group administered with the mutated MCP-1 gene (7ND-MCP-1 gene) as opposed to 186.75±130.78 µmol/g-rat liver weight) in the control group. A significant lowering effect on the hydroxyproline in the liver tissue by the administration of the mutated MCP-1 gene (7ND-MCP-1 gene) was hence observed.

INDUSTRIAL APPLICABILITY

As evident from the Example, the MCP-1 function inhibitors are useful as preventives and/or remedies for liver diseases such as hepatic fibrosis and cirrhosis.

---

The invention claimed is:

1. A method of reducing fibrosis in a fibrotic liver of a mammal in need thereof, comprising
administering intramuscularly into the mammal in need thereof a nucleic acid comprising SEQ ID NO: 1,
wherein the nucleic acid of SEQ ID NO: 1 encodes a dominant negative form of MCP1, and
wherein the nucleic acid of SEQ ID NO: 1 is operably linked to a promoter, thereby expressing the nucleic acid of SEQ ID NO: 1 in a muscle of the mammal in need thereof and reducing the amount of fibrosis in the fibrotic liver of the mammal in need thereof.

2. The method of claim 1, wherein the nucleic acid of SEQ ID NO: 1 that is operably linked to a promoter is integrated into an expression vector, and wherein the expression vector is selected from the group consisting of a plasmid vector, a and a virus vector.

3. The method of 1, wherein the nucleic acid of SEQ ID NO: 1 which is operably linked to a promoter is integrated into an expression vector; and wherein the expression vector is selected from the group consisting of pcDNA3, pEF-BOS, pXT1, adenovirus vector, and Sendai virus vector.

4. The method of claim 1, wherein the nucleic acid of SEQ ID NO: 1 is present in an amount of from 0.01 to 100 mg.

5. The method of claim 1, wherein the promoter is selected from the group consisting of an SV40 promoter, a CMV promoter, HSV-TK, SRα and RSV.

6. The method of claim 1, wherein the administering is repeated at least one time, and wherein the at least one additional administration is performed from 2 to 4 weeks after the first administration.

7. The method of claim 1, wherein the method further comprises injecting the nucleic acid of SEQ ID NO: 1 with at least one additive.

8. The method of claim 7, wherein the at least one additive is selected from the group consisting of an isotonic solution, a buffer, a preservative, an excipient, a soothing agent, and combinations thereof.

9. The method of claim 1, wherein the method further comprises injecting the nucleic acid of SEQ ID NO: 1 with liposomes, and
wherein the liposomes each comprise a lipid bilayer.

10. The method of claim 9, wherein the nucleic acid of SEQ ID NO: 1 is inside the lipid bilayers of at least some of the liposomes.

11. The method of claim 9, wherein nucleic acid of SEQ ID NO: 1 is outside the lipid bilayers of the liposomes.

12. The method of claim 9, wherein the nucleic acid of SEQ ID NO: 1 is divided such that some of the nucleic acid of SEQ ID NO: 1 is outside of the lipid bilayers of the liposomes, and the remainder of the nucleic acid of SEQ ID NO: 1 is inside the lipid bilayer of at least some of the liposomes.

* * * * *

UNITED STATES PATENT AND TRADEMARK OFFICE
CERTIFICATE OF CORRECTION

PATENT NO. : 7,335,647 B2
APPLICATION NO. : 10/398285
DATED : February 26, 2008
INVENTOR(S) : Kensuke Egashira et al.

It is certified that error appears in the above-identified patent and that said Letters Patent is hereby corrected as shown below:

Column 1, Claim 1, line 32, "MCP1" should read --MCP-1--

Column 1, Claim 2, line 41-42, "a plasmid vector, a and a virus vector" should read --a plasmid vector, and a virus vector--

Signed and Sealed this

Twenty-fourth Day of November, 2009

David J. Kappos
*Director of the United States Patent and Trademark Office*

SEQUENCE LISTING

<160> NUMBER OF SEQ ID NOS: 2

<210> SEQ ID NO 1
<211> LENGTH: 279
<212> TYPE: DNA
<213> ORGANISM: Homo sapiens

<400> SEQUENCE: 1
atgaaagtct ctgccgccct tctgtgcctg ctgctcatag cagccacctt cattccccaa    60

-continued

```
gggctcgctc aggtcacctg ctgttataac ttcaccaata ggaagatctc agtgcagagg       120
ctcgcgagct atagaagaat caccagcagc aagtgtccca aagaagctgt gatcttcaag       180
accattgtgg ccaaggagat ctgtgctgac cccaagcaga agtgggttca ggattccatg       240
gaccacctgg acaagcaaac ccaaactccg aagacttga                              279

<210> SEQ ID NO 2
<211> LENGTH: 300
<212> TYPE: DNA
<213> ORGANISM: Homo sapiens

<400> SEQUENCE: 2
atgaaagtct ctgccgccct tctgtgcctg ctgctcatag cagccacctt cattccccaa        60
gggctcgctc agccagatgc aatcaatgcc ccagtcacct gctgttataa cttcaccaat       120
aggaagatct cagtgcagag gctcgcgagc tatagaagaa tcaccagcag caagtgtccc       180
aaagaagctg tgatcttcaa gaccattgtg gccaaggaga tctgtgctga ccccaagcag       240
aagtgggttc aggattccat ggaccacctg gacaagcaaa cccaaactcc gaagacttga       300
```